United States Patent
Shimizu

(10) Patent No.: US 9,719,840 B2
(45) Date of Patent: Aug. 1, 2017

(54) BODY WEIGHT MANAGEMENT DEVICE FOR MANAGING A MEASUREMENT SUBJECT'S BODY WEIGHT USING A TARGET

(75) Inventor: Satoe Shimizu, Kyoto (JP)

(73) Assignee: OMRON HEALTHCARE CO., LTD., Muko-shi (JP)

( * ) Notice: Subject to any disclaimer, the term of this patent is extended or adjusted under 35 U.S.C. 154(b) by 152 days.

(21) Appl. No.: 14/342,910

(22) PCT Filed: Jun. 8, 2012

(86) PCT No.: PCT/JP2012/064757
§ 371 (c)(1),
(2), (4) Date: Mar. 5, 2014

(87) PCT Pub. No.: WO2013/046809
PCT Pub. Date: Apr. 4, 2013

(65) Prior Publication Data
US 2014/0212850 A1    Jul. 31, 2014

(30) Foreign Application Priority Data
Sep. 26, 2011  (JP) .................... 2011-208662

(51) Int. Cl.
*A61B 5/00* (2006.01)
*G01G 19/414* (2006.01)
(Continued)

(52) U.S. Cl.
CPC ....... *G01G 19/4146* (2013.01); *A61B 5/0537* (2013.01); *G01G 19/44* (2013.01); *G01G 19/50* (2013.01); *A61B 5/4872* (2013.01)

(58) Field of Classification Search
CPC ...... G01G 19/414; G01G 19/40; G01G 19/44; G01G 19/00; A61B 5/053; A61B 5/103
(Continued)

(56) References Cited

U.S. PATENT DOCUMENTS 4,576,244 A * 3/1986 Zeigner .................. G01G 19/44
                                                                177/245
4,629,015 A * 12/1986 Fried ...................... A61M 1/16
                                                                128/DIG. 13
(Continued)

FOREIGN PATENT DOCUMENTS

CN        101680799 A        3/2010
JP      A 2005-218582        8/2005
(Continued)

OTHER PUBLICATIONS

Jul. 10, 2012 Search Report issued in International Patent Application No. PCT/JP2012/064757 (with translation).
(Continued)

Primary Examiner — Robert J Utama
(74) Attorney, Agent, or Firm — Oliff PLC

(57) ABSTRACT

A body weight management device includes: a change obtainment unit for obtaining an intra-day body weight change value on a daily basis based body weight measurement values of a measurement subject measured on a daily basis; an achievement rate obtainment unit for comparing the intra-day body weight change value obtained by the change obtainment unit with an intra-day target weight loss value and obtaining, based on a result of the comparison, a target achievement rate indicating a percentage of total days in a predetermined period in which the intra-day body weight change value has reached the intra-day target weight loss value; and a target obtainment unit for obtaining, based on the target achievement rate obtained by the achievement rate obtainment unit, a new intra-day target weight loss value to serve as a target for future body weight measurement.

12 Claims, 12 Drawing Sheets

(51) Int. Cl.
  *G01G 19/50* (2006.01)
  *A61B 5/053* (2006.01)
  *G01G 19/44* (2006.01)

(58) Field of Classification Search
  USPC .......................................................... 434/238
  See application file for complete search history.

(56) References Cited

U.S. PATENT DOCUMENTS

| | | | |
|---|---|---|---|
| 6,369,337 B1* | 4/2002 | Machiyama | A61B 5/0537 177/245 |
| 8,538,772 B2* | 9/2013 | Sato et al. | 705/2 |
| 8,541,700 B2* | 9/2013 | Sato et al. | 177/25.19 |
| 2002/0022773 A1* | 2/2002 | Drinan | A61B 5/0537 600/300 |
| 2004/0035611 A1* | 2/2004 | Honda | A61B 5/0537 177/25.19 |
| 2004/0238228 A1* | 12/2004 | Montague | G01G 19/44 177/25.13 |
| 2008/0004501 A1* | 1/2008 | Gavrilov | G01G 19/4146 600/300 |
| 2009/0118589 A1* | 5/2009 | Ueshima | A61B 5/0002 600/300 |
| 2010/0130831 A1* | 5/2010 | Sato | G01G 23/3728 600/300 |
| 2011/0106553 A1* | 5/2011 | Sato | A61B 5/0537 705/2 |
| 2011/0143322 A1* | 6/2011 | Tsang | G06F 19/3475 434/127 |
| 2012/0004570 A1* | 1/2012 | Shimizu | A61B 5/0537 600/547 |
| 2013/0131463 A1* | 5/2013 | Date | G01G 19/50 600/301 |
| 2014/0212850 A1* | 7/2014 | Shimizu | G01G 19/50 434/127 |

FOREIGN PATENT DOCUMENTS

| | | |
|---|---|---|
| JP | A 2007-226775 | 9/2007 |
| JP | A 2008-304421 | 12/2008 |
| JP | A 2009-50523 | 3/2009 |
| JP | A 2010-181377 | 8/2010 |
| JP | A 2010-237805 | 10/2010 |

OTHER PUBLICATIONS

Mar. 20, 2015 Office Action issued in Chinese Application No. 201280046469.8.

* cited by examiner

FIG. 5A

| MEASURED BODY WEIGHT 401 | LOSS AMOUNT 402 | MEASUREMENT DATE/TIME 403 | IMPEDANCE 404 |
|---|---|---|---|
| 60.0kg | 82.3g | 2009/1/29 23:12 | ××Ω |
| 57.7kg | 83.4g | 2009/1/30 23:10 | ×△Ω |
| ⋮ | ⋮ | ⋮ | ⋮ |

FIG. 5B

| INTRA-DAY TARGET WEIGHT LOSS VALUE | 41 |
|---|---|
| 40g | |

FIG. 5C

| TARGET SETTING DAY | 42 |
|---|---|
| 2009/1/20 | |

FIG. 5D

| LONG-TERM TARGET WEIGHT GAIN/LOSS AMOUNT | 43 |
|---|---|
| -4kg | |

FIG. 5E

| TARGET ACHEIVEMENT PERIOD | 44 |
|---|---|
| 3 MONTH | |

FIG. 5F

| INITIAL BODY WEIGHT | 45 |
|---|---|
| 60.0kg | |

FIG. 5G

| ANALYSIS PROCESS EXECUTION DAY | 46 |
|---|---|
| 2009/2/10 | |

BODY WEIGHT MANAGEMENT DEVICE FOR MANAGING A MEASUREMENT SUBJECT'S BODY WEIGHT USING A TARGET

TECHNICAL FIELD

This invention relates to body weight management devices, and particularly relates to body weight management devices for managing a measurement subject's body weight using a target value.

BACKGROUND ART

Body weight management techniques that aim to reduce weight in order to prevent obesity have been in demand for some time. For example, Patent Literature 1 (JP 2010-181377A) and Patent Literature 2 (JP 2008-304421A) disclose devices that calculate target values based on intra-day body weight changes. In Patent Literature 3 (JP 2007-226775A), meanwhile, the deviation of an actual body weight from a target body weight is calculated on a daily basis. Finally, in Patent Literature 4 (JP 2010-237805A), a target weight loss amount is calculated using the formula (current body weight)−(target body weight).

CITATION LIST

Patent Literature

Patent Literature 1: JP 2010-181377A
Patent Literature 2: JP 2008-304421A
Patent Literature 3: JP 2007-226775A
Patent Literature 4: JP 2010-237805A

SUMMARY OF INVENTION

Technical Problem

The techniques of the aforementioned Patent Literature 1-4 do not obtain targets based on the actual pace of the measurement subject's weight loss. If, for example, the target is a daily weight loss value, whether or not the measurement subject achieves that target is easily affected by the measurement subject's daily routines, mood, and so on. Specifically, while the measurement subject can easily reach his/her goals during periods where s/he keeps a regular daily routine, it is difficult to achieve the same targets during periods where his/her daily routine is irregular. However, because the daily targets are determined without consideration for the degree to which the measurement subject has achieved his/her targets in Patent Literature 1-4, it is easy for the measurement subject to achieve his/her targets when his/her daily routine is regular but difficult for the measurement subject to achieve his/her targets when his/her daily routine is irregular; as a result, it is difficult for the measurement subject to stay motivated to lose weight.

Accordingly, it is an object of this invention to provide a body weight management device that, based on a past target achievement rate for intra-day target weight loss values, obtains a new intra-day target weight loss value for future body weight measurement.

Solution to Problem

A body weight management device according to an aspect of the invention includes: a change obtainment unit for obtaining an intra-day body weight change value on a daily basis based on body weight measurement values of a measurement subject measured on a daily basis; an achievement rate obtainment unit for comparing the intra-day body weight change value obtained by the change obtainment unit with an intra-day target weight loss value and obtaining, based on a result of the comparison, a target achievement rate indicating a percentage of days, in a total number of days in a predetermined period, in which the intra-day body weight change value has reached the intra-day target weight loss value; and a target obtainment unit for obtaining, based on the magnitude of a difference between the target achievement rate obtained by the achievement rate obtainment unit and a threshold, a new intra-day target weight loss value to serve as a target for future body weight measurement.

Advantageous Effects of Invention

According to the present invention, a target for future body weight measurement can be obtained based on a past target achievement rate for the intra-day target weight loss value.

BRIEF DESCRIPTION OF DRAWINGS

FIGS. 5A through 5G are diagrams illustrating various types of data held in a storage unit according to an embodiment of the present invention.

DESCRIPTION OF EMBODIMENTS

Figure 1:
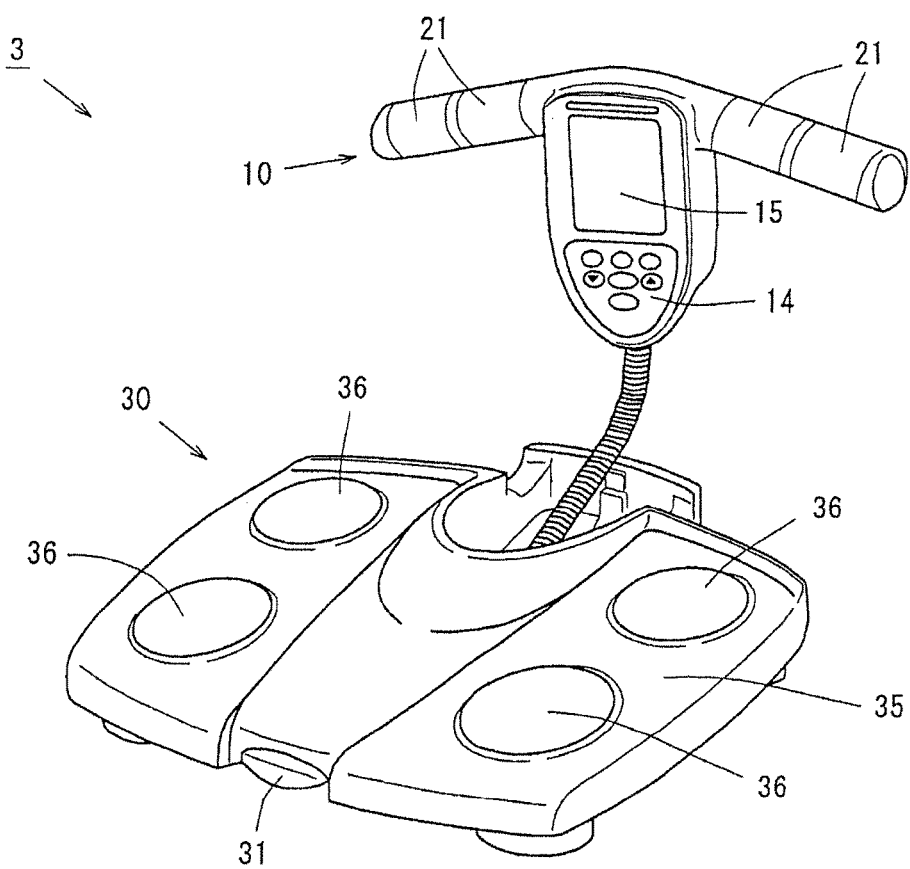
FIG. 1 is a perspective view illustrating the external appearance of a body composition meter according to an embodiment of the present invention.

Hereinafter, an embodiment of the present invention will be described in detail with reference to the drawings. Note that in the following embodiment, identical or corresponding elements are given the same reference numerals in the drawings, and descriptions thereof will not be repeated.

First, definitions will be given for terms. In the present embodiment, "morning time" refers, with respect to body weight measurement, to a period of time spanning from, for example, 4 AM to noon (12 PM), whereas "evening time" refers to a period of time spanning from, for example, 7 PM to 2 AM. "Morning body weight" refers to a body weight measured during the morning time, whereas "evening body weight" refers to a body weight measured during the evening time. To simplify the descriptions, it is assumed that the body weight (evening body weight) is measured immediately before going to bed, and that the body weight (morning body weight) is measured immediately after waking up.

Here, "intra-day" refers to a single day spanning from when a measurement subject rises to the next time the measurement subject rises, or spanning from when the measurement subject goes to sleep to the next time the measurement subject goes to sleep. "Intra-day body weight change value" thus refers to a change in the measurement subject's body weight within a single day. Likewise, "intra-day target weight loss value" refers to a weight loss amount to serve as an target within a single day.

In the present embodiment, a body weight/body composition meter capable of obtaining not only a body weight but also body composition information, such as a body fat percentage, by measuring a body impedance (called simply "impedance" hereinafter), is illustrated as an example of a body weight management device, but a device that only has a function for measuring a body weight may be employed as well. In such a case, the impedance is assumed to be received from a separate measurement device.

Figure 2:
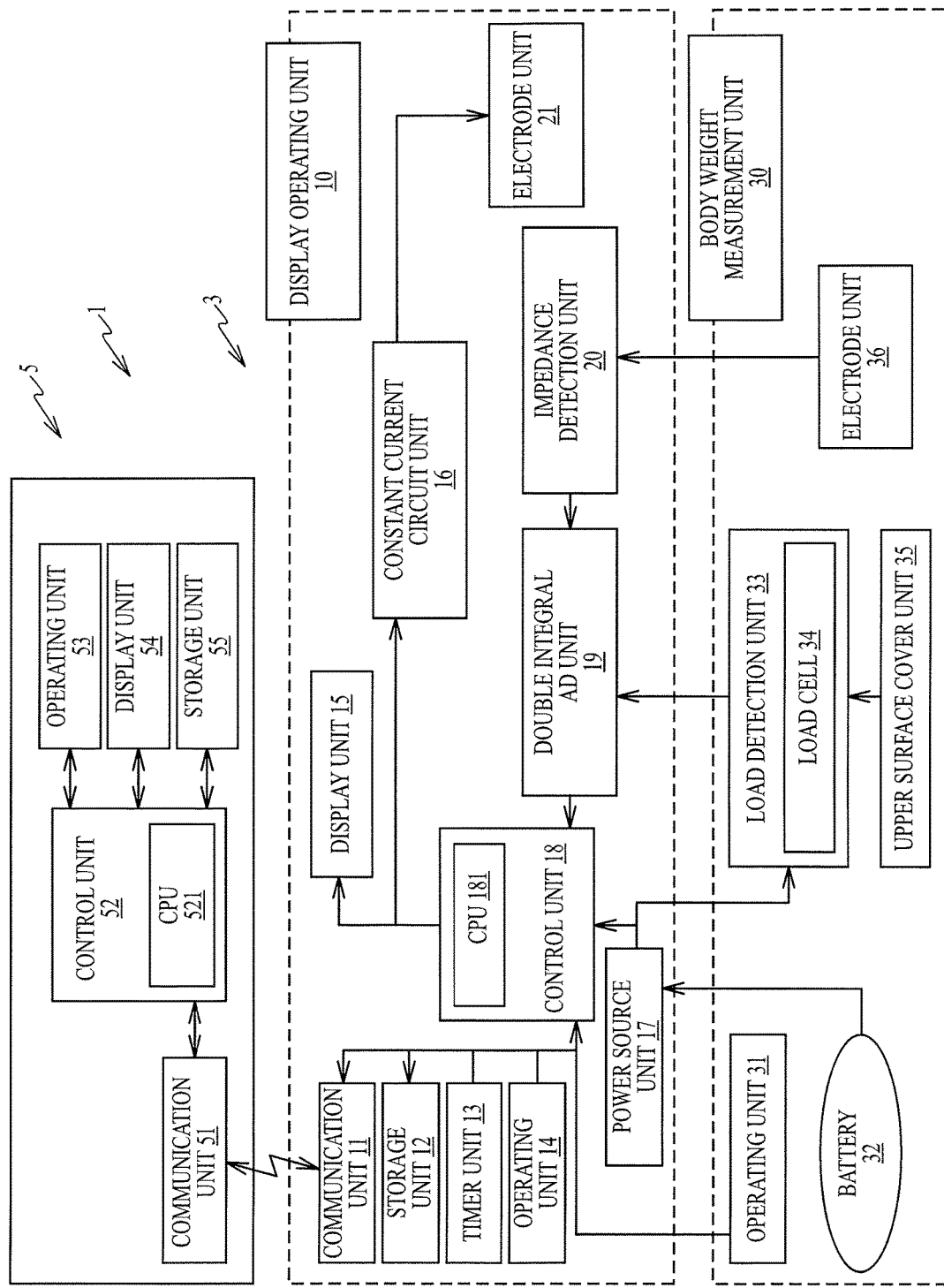
FIG. 2 is a block diagram illustrating the configuration of the body composition meter and a server according to an embodiment of the present invention.
Figure 3:
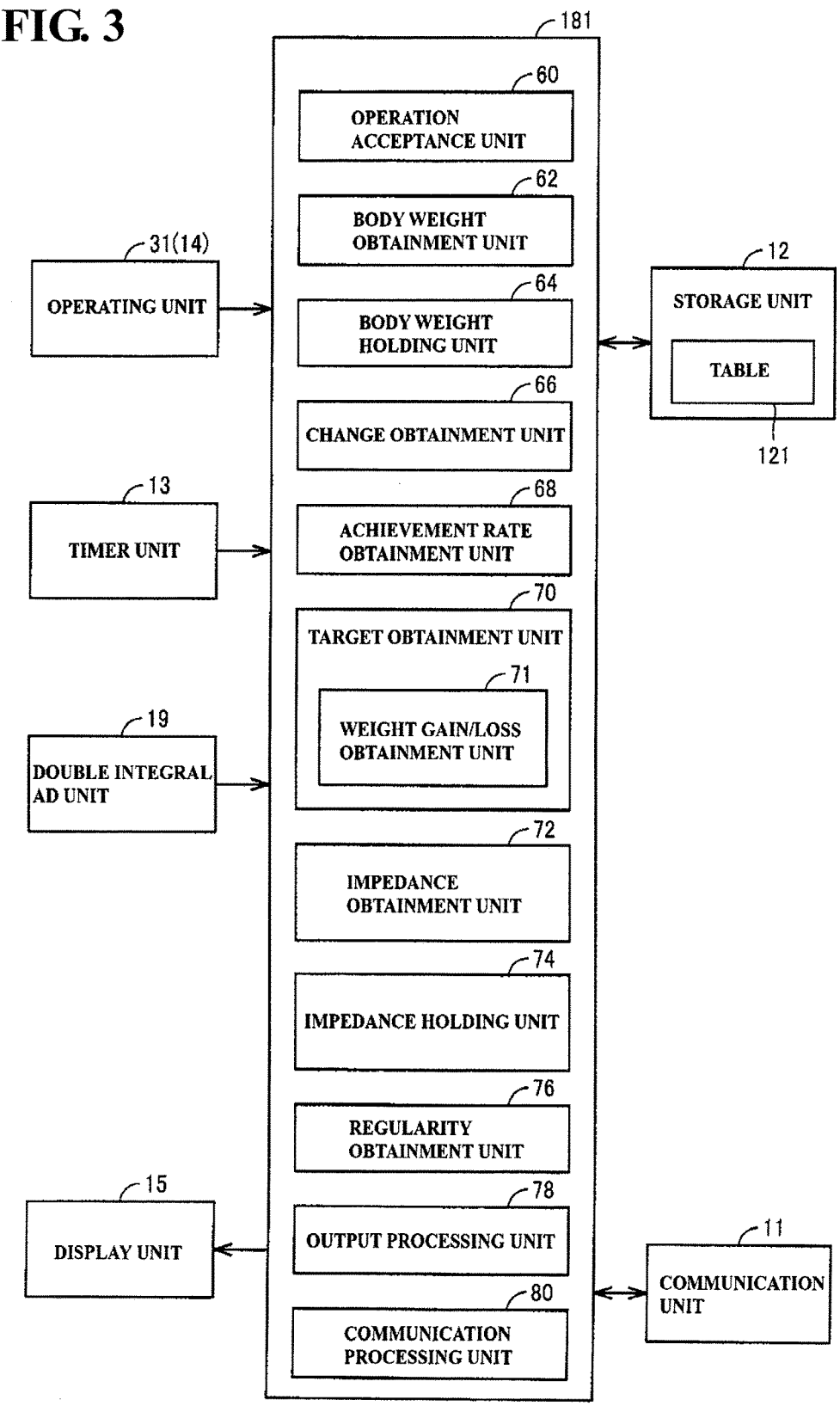
FIG. 3 is a diagram illustrating a functional configuration for body weight management provided in a body weight/body composition meter according to an embodiment of the present invention.
Figure 4:
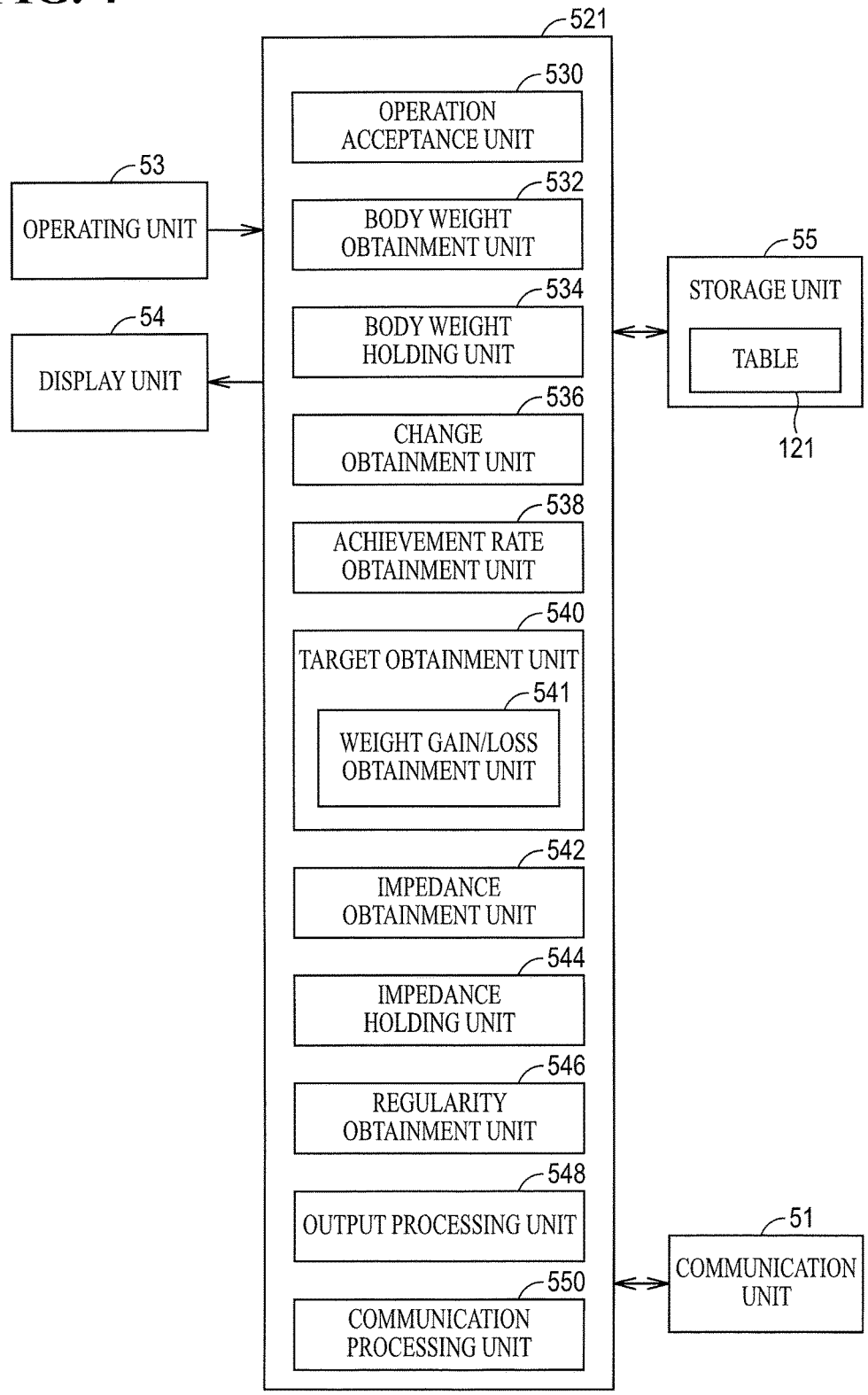
FIG. 4 is a diagram illustrating a functional configuration for body weight management provided in a server according to an embodiment of the present invention.

FIG. 1 illustrates the external appearance of a body weight/body composition meter 3, whereas FIG. 2 illustrates the configuration of a body weight management system 1 including a server 5. FIGS. 3 and 4 illustrate the functional configurations of the body weight/body composition meter 3 and the server 5.

The body weight management system 1 shown in FIG. 2 includes the body weight/body composition meter 3 and the server (server computer) 5 that communicates with the body weight/body composition meter 3. To simplify the descriptions, FIG. 2 illustrates a single weight/body composition meter 3 being connected to the server 5, but multiple weight/body composition meters 3 may be connected. In FIG. 2, the body weight/body composition meter 3 and the server 5 communicate wirelessly or over wires. Note that the exchange of data between the body weight/body composition meter 3 and the server 5 is not limited to communications, and the exchange may take place via a storage medium.

As shown in FIG. 1, the body weight/body composition meter 3 includes a display/operating unit 10, which is a first housing member that a measurement subject holds with his/her hands, and a body weight measurement unit 30, which is a second housing member onto which the measurement subject steps.

The display/operating unit 10 includes, as shown in FIG. 2, a communication unit 11, a storage unit 12, a timer unit 13, an operating unit 14, a display unit 15, a constant current circuit unit 16, a power source unit 17, a control unit 18 that includes a CPU (central processing unit) 181, a double integral AD (analog/digital) unit 19, an impedance detection unit 20, and electrode units 21.

The communication unit 11 is connected to the control unit 18, and communicates with the server 5 in accordance with a control signal from the control unit 18. Note that the communication unit 11 is not limited to communicating with the server 5; the communication unit 11 may communicate with any appropriate device, including another body information obtainment device such as a pedometer or the like, or a personal computer, mobile information terminal (a PDA (personal digital assistant), a mobile telephone, or the like), and so on.

The storage unit 12 includes an apparatus that can store information, such as a non-volatile memory, a hard disk, or the like. The storage unit 12 has information read out therefrom and written thereto in accordance with a control signal from the control unit 18, to which the storage unit 12 is connected.

The timer unit 13 is a device configured of a timer or counter that measures the present day/time or the like, and outputs that time to the control unit 18.

The operating unit 14 includes multiple buttons or switches and the like (see FIG. 1) that are operated by being depressed or the like. By manipulating the operating unit 14, the measurement subject can input his/her personal information and body information, such as a personal identifier, sex, age, height, body weight, and so on. The inputted information is provided to the control unit 18.

The display unit 15 is configured of a display device such as a liquid-crystal display (see FIG. 1), and displays images such as text, graphics, or the like in accordance with an image signal supplied from the control unit 18. The constant current circuit unit 16 applies a high-frequency (AC) current supplied from the power source unit 17 to current application electrode units 21 in a single direction, under the control of the control unit 18. The power source unit 17 supplies operational electricity to the respective elements, including the control unit 18.

The control unit 18 is configured of the CPU 181 and a microcomputer that includes a ROM (read-only memory) and a RAM (random access memory) that are not shown, and executes operations for controlling the respective elements, computation operations, and so on in accordance with programs and data stored in the ROM or the like. These programs and data include programs and data for body weight management.

The double integral AD unit 19 is a double integral-type AD conversion unit. During operations, the double integral AD unit 19 converts an analog signal (a voltage signal) outputted from the impedance detection unit 20 into a digital signal and outputs that digital signal to the control unit 18.

The impedance detection unit 20 detects an impedance of the measurement subject based on a potential difference between electrode units 36 provided in the body weight measurement unit 30 and the electrode units 21 provided in the display/operating unit 10.

The electrode units 21 are provided on the surfaces of grip portions (see FIG. 1) in the display/operating unit 10, which are held in the measurement subject's hand. The electrode units 21 apply the high-frequency (AC) current, supplied from the power source unit 17, to the palms of the measurement subject's hands that are gripping the grip portions.

The body weight measurement unit 30 includes an operating unit 31, a battery 32, a load detection unit 33, and the electrode units 36. The operating unit 31 functions as an input switch that is manipulated in order to switch the power on or off, and when the operating unit 31 is manipulated, an input signal is outputted to the control unit 18 in response to that manipulation. The battery 32 supplies power to the respective elements, and in particular, to the power source unit 17.

The load detection unit 33 has multiple load cells 34 provided therein. The load detection unit 33 measures the body weight of the measurement subject that has stepped onto an upper surface cover unit 35 (see FIG. 1) that also serves as an upper surface cover of the housing member. The measured body weight is outputted to the double integral AD unit 19.

The electrode units 36 are provided in the surface of the upper surface area of the body weight measurement unit 30 (see FIG. 1) onto which the measurement subject steps, and serve as current measurement electrodes that detect a current that flows from the soles of the measurement subject's feet. The electrode units 36 include four electrodes that make contact with the left toe side, the left heel side, the right toe side, and the right heel side of the measurement subject's feet.

Each of the load cells 34 in the load detection unit 33 is disposed so as to be capable of measuring a load placed on the upper surface area of the body weight measurement unit 30, and here, are disposed below the respective electrodes of the electrode units 36. Accordingly, both the impedance and the body weight can be measured simultaneously when the measurement subject steps upon the upper surface area.

During body weight measurement, a load produced by the measurement subject's body weight is exerted on the load cells 34. Each of the load cells 34 is configured of a deforming member, formed of a metal member that deforms in response to a load exerted thereon, and a strain gauge that is applied to the deforming member. When the deforming member bends, the strain gauge extends/contracts, and a resistance value changes in accordance with the extension/contraction of the strain gauge; the change in resistance is then derived as a load signal output. Accordingly, in the case where the measurement subject has stepped onto the upper surface area and both feet have been placed on the load cells 34, the deforming member will bend due to the measurement subject's body weight that has been applied to the load cells 34, and the body weight will be measured as a change in the aforementioned load signal output.

Although the load cells 34 are used in the present embodiment as load sensors for detecting a load, it should be noted that a sensor that employs, for example, springs, a piezoelectric film, or the like, a compression element, a displacement sensor, or the like may be used as long as that element is capable of detecting the amount of a force applied to the upper surface area.

The server 5 includes communication unit 51, a control unit 52, an operating unit 53, a display unit 54, and a storage unit 55. The control unit 52 is configured of a computer including a CPU 521, a ROM (read-only memory), a RAM (random access memory).

The communication unit 51 exchanges data with the body weight/body composition meter 3 under the control of the control unit 52. The CPU 521 of the control unit 52 controls the operations of the respective elements and executes various types of computations in accordance with programs and data stored in the ROM or the like.

The operating unit 53 includes a keyboard, a mouse, or the like. Signals inputted as a result of operations performed by an operator are outputted to the control unit 52.

The display unit 54 corresponds to a liquid-crystal display, a CRT (cathode ray tube) display, or the like. The display unit 54 displays images such as graphics, text, or the like in accordance with a control signal supplied from the control unit 52.

The storage unit 55 corresponds to a fixed storage device such as a hard disk, or a recording medium that can be read by the computer that includes the CPU 521, such as a flexible disk, a CD-ROM (compact disk read-only memory), a ROM (read-only memory), a RAM (random access memory), a memory card, and so on.

The storage unit 55 stores data measured by the body weight/body composition meter 3 (body composition information, body weight data, measurement day/time data, and so on), and various types of data related to the measurement subject, including the personal information such as the measurement subject's name (identifier), address, and so on, as well as the body information (sex, height, age, and the like).

The functional configuration of the body weight/body composition meter 3, as related to body weight management, will be described with reference to FIG. 3. FIG. 3 illustrates functions of the CPU 181 as well as peripheral circuitry related thereto.

The CPU 181 includes an operation acceptance unit 60 that accepts a user operation via the operating unit 31 or 14 and outputs an operation signal based on the accepted operation; a body weight obtainment unit 62 that obtains body weight data including a body weight measurement value and the date/time of the measurement; a body weight holding unit 64 for holding the obtained body weight data in a predetermined region of the storage unit 12; a change obtainment unit 66; an achievement rate obtainment unit 68; a target obtainment unit 70 having a weight gain/loss obtainment unit 71; an impedance obtainment unit 72; an impedance holding unit 74; a regularity obtainment unit 76 for obtaining information expressing how regular the measurement subject's daily lifestyle is; an output processing unit 78 for displaying information in the display unit 15; and a communication processing unit 80 for communicating with external devices, including the server 5, via the communication unit 11.

The change obtainment unit 66 obtains the intra-day body weight change value based on the measurement subject's daily body weight measurement values. The achievement rate obtainment unit 68 compares the intra-day body weight change value obtained by the change obtainment unit 66 with the intra-day target weight loss value, and obtains a target achievement rate based on a result of the comparison. Here, the "target achievement rate" indicates a percentage of days, in a total number of days in a predetermined past period held in the storage unit 12, in which the intra-day body weight change value has reached the intra-day target weight loss value.

Based on the target achievement rate obtained by the achievement rate obtainment unit 68, the target obtainment unit 70 obtains a new intra-day target weight loss value to serve as a target for future body weight measurement. To be more specific, upon obtaining a weight gain/loss amount for the intra-day target weight loss value based on the target achievement rate, the weight gain/loss obtainment unit 71 calculates the new intra-day target weight loss value to serve as a target for future body weight measurement using the intra-day target weight loss value employed in the comparison and the obtained weight gain/loss amount.

The impedance obtainment unit 72 obtains impedance data containing impedance values of the measurement subject, and the impedance holding unit 74 holds the impedance data obtained by the impedance obtainment unit 72 in the storage unit 12. Here, the measurement subject's body impedance is assumed to be measured every set time, such as the evening time when a daily body weight measurement is taken.

These elements are realized by programs executed by the CPU 181. These programs are stored in advance in the ROM (not shown) of the control unit 18. The functions of the respective elements are realized by the CPU 181 reading out the programs from the ROM and executing the commands in the read-out programs. The programs may be downloaded by the communication unit 11 from an external device such as the server 5, stored in the storage unit 12, and read out from the storage unit 12 and executed by the CPU 181.

A body weight management function according to the present embodiment may be implemented by the CPU 521 of the server 5 that has the functions shown in FIG. 4. Details of the server 5 in FIG. 4 will be given later.

The various types of data held in the storage unit 12 will be described with reference to FIGS. 5A through 5G. In the case where the body weight/body composition meter 3 is shared among multiple measurement subjects, the data shown in FIG. 5 is stored on a measurement subject-by-measurement subject basis. Here, however, it is assumed, for the sake of simplicity, that only a single measurement subject is using the body weight/body composition meter 3. Furthermore, it is assumed that the evening body weight is measured once a day.

Each time the measurement subject's body weight is measured by the body weight measurement unit 30, measurement data 40 as indicated in FIG. 5A is stored in the storage unit 12. Accordingly, one instance of measurement data 40 is stored every day. The storage unit 12 has a capacity that enables multiple weeks' worth or multiple months' worth of the measurement data 40 to be stored.

The measurement data 40 includes data 401 indicating an actually-measured evening body weight value, loss amount data 402 calculated according to the formula (yesterday's evening body weight)−(today's evening body weight), data 403 indicating the date/time of the measurement based on time measurement data from the timer unit 13, and data 404 indicating a measured impedance value, with the pieces of data being associated with one another. The data 401 and 403 indicate the aforementioned body weight data, whereas the data 404 indicates the aforementioned impedance data.

The loss amount data 402 is obtained by the change obtainment unit 66 and stored in the storage unit 12. Each time the body weight is measured, the change obtainment unit 66 subtracts the evening body weight value in the data 401 obtained through the present body weight measurement from the evening body weight value in the data 401 obtained through the previous (that is, yesterday's) body weight measurement stored in the storage unit 12, and obtains a value resulting from the subtraction as the loss amount data 402.

Although the data 404 is described as being an impedance value measured by the impedance detection unit 20, the method for obtaining the data 404 is not limited thereto. For example, the impedance may be measured using a separate device, and the measured value may be received by the communication processing unit 80 via the communication unit 11 and stored in the storage unit 12. Alternatively, a value inputted by the measurement subject through the operating unit 14 (or the operating unit 31) may be stored in the storage unit 12 as the data 404.

Intra-day target weight loss value data 41, shown in FIG. 5B, indicates an intra-day weight loss amount value serving as a weight loss target for the measurement subject to achieve. In the present embodiment, the evening body weight is measured every day, and thus the intra-day target weight loss value data 41 indicates a target value for the loss amount data 402, calculated according to the formula (yesterday's evening body weight)−(today's evening body weight). The intra-day target weight loss value data 41 is varied by the target obtainment unit 70.

Target setting day data 42 is indicated in FIG. 5C. The target setting day data 42 indicates the date at which the measurement subject started body weight management, such as going on a diet, using the body weight/body composition meter 3. In other words, this data indicates the date at which the measurement subject set (inputted) the data shown in FIGS. 5B through 5G for the purpose of body weight management.

Long-term target weight gain/loss amount data 43, shown in FIG. 5D, indicates a target value for a weight gain/loss amount, inputted by the measurement subject manipulating the operating unit 14. In the present embodiment, the purpose of body weight management is losing weight, and thus a negative value (for example, −4 kg) is inputted.

Target achievement period data 44, shown in FIG. 5E, holds a target achievement period set by the measurement subject manipulating the operating unit 14. The target achievement period is a target value for an amount of time it will take to lose the weight indicated by the long-term target weight gain/loss amount data 43 (for example, three months).

The CPU 181 determines, as appropriate, whether or not an intra-day weight gain/loss amount that serves as a daily norm, obtained by dividing the value of the long-term target weight gain/loss amount data 43 by the number of days in the target achievement period data 44, falls within a predetermined range. In the case where it is determined that the amount is outside of the predetermined range, an error display is made in the display unit 15 via the output processing unit 78. The measurement subject is then prompted to re-input the target achievement period until the amount is determined to fall within the predetermined range. Through this, excessive weight loss that places a burden on the measurement subject's body can be avoided.

The intra-day weight gain/loss amount determined to be appropriate is stored in the storage unit 12 as the intra-day target weight loss value data 41. Here, 40 g is set for an initial value of the intra-day target weight loss value data 41.

With respect to body weight changes, experiments performed by the inventors indicate that for a healthy adult, a weight loss (or gain) for one month that is a loss/gain percentage of the present body weight within the predetermined range, or in other words, within 2% to 10%, will not be unhealthy. Accordingly, the present embodiment is set so that the loss amount over one month is an amount that is 2% to 10% of the present body weight.

Initial body weight data 45, shown in FIG. 5F, indicates a body weight measured on the initial date/time when the body weight management such as a diet was started, or in other words, indicates the body weight measured on the date specified by the target setting day data 42.

Through this, a body weight obtained by adding the long-term target weight gain/loss amount data 43 to the initial body weight data 45 corresponds to the target body weight at a target date when the body weight management, such as the diet, is complete (that is, a date obtained by adding the target achievement period data 44 to the target setting day data 42).

Analysis process execution day data 46, indicated in FIG. 5G, is obtained by the CPU 181 as a date, based on time data from the timer unit 13, on which an analysis process (mentioned later; see step S11 in FIG. 6) is executed, each time that process is executed; the analysis process execution day data 46 is stored in the storage unit 12. Accordingly, the analysis process execution day data 46 indicates the most recent date when the analysis process has been executed. Note that it is assumed that null data is set for an initial value of the analysis process execution day data 46.

Figure 6:
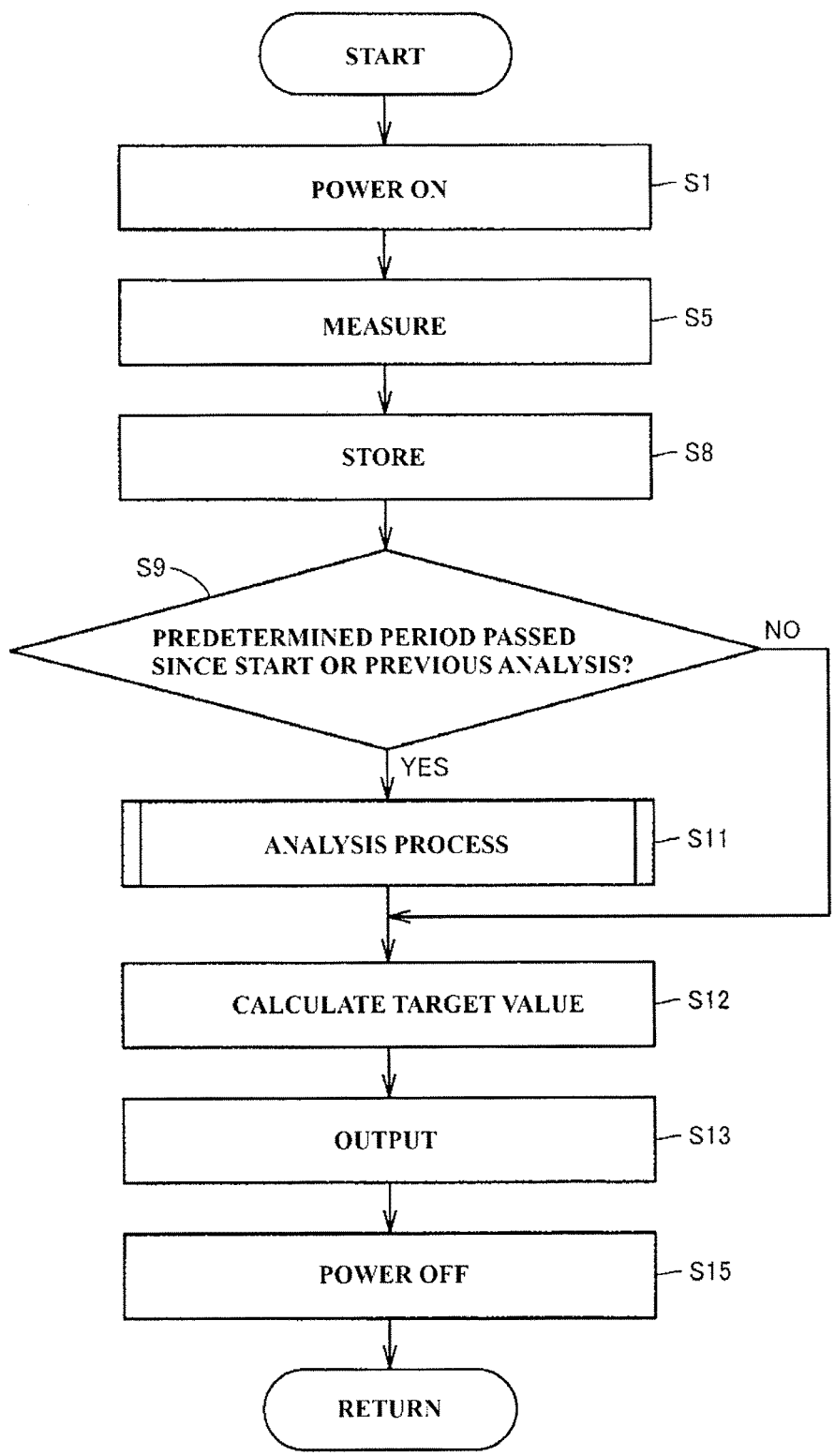
FIG. 6 is a main flowchart according to an embodiment of the present invention.
Figure 7:
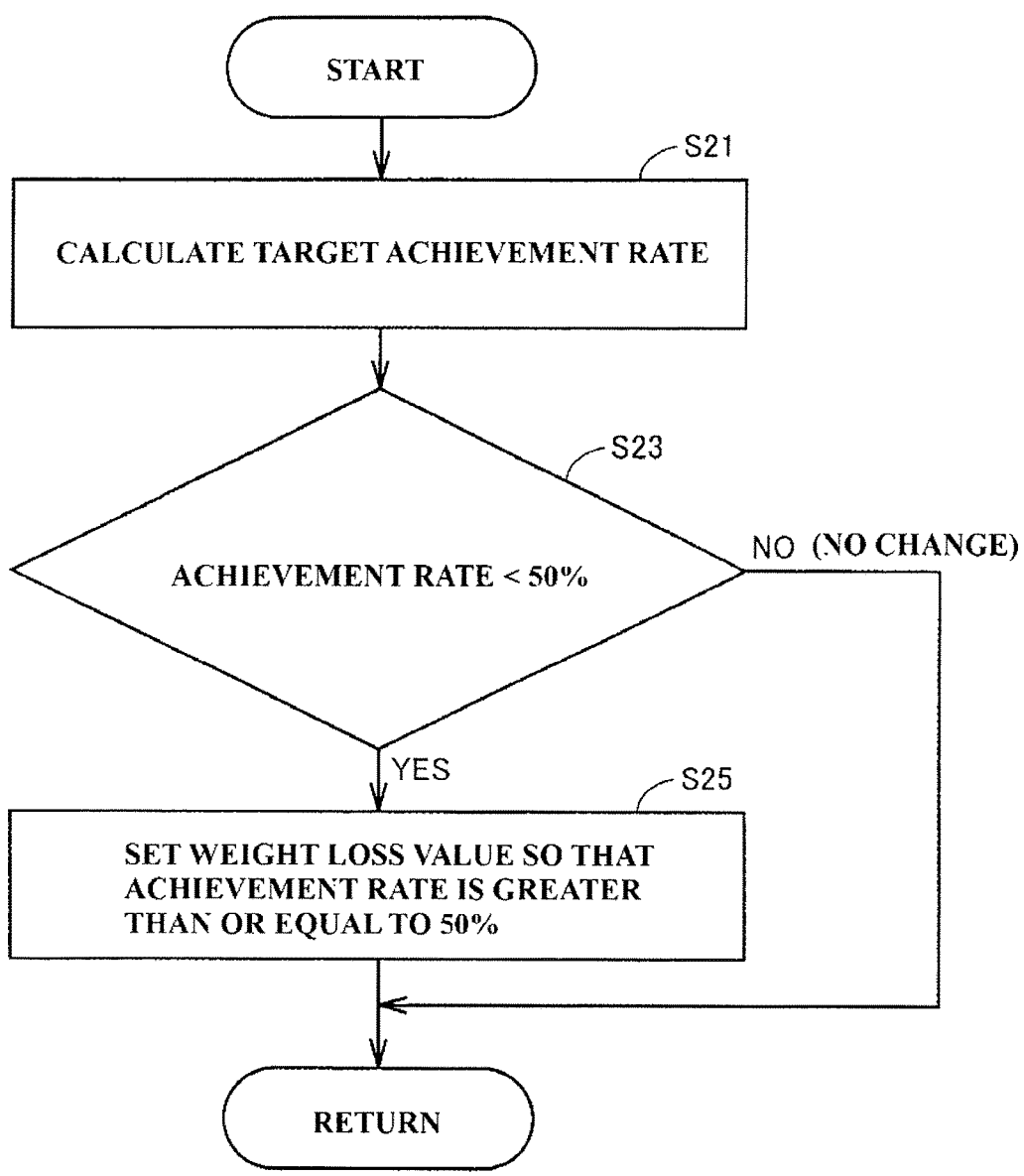
FIG. 7 is a flowchart illustrating an analysis process according to an embodiment of the present invention.
Figure 8:
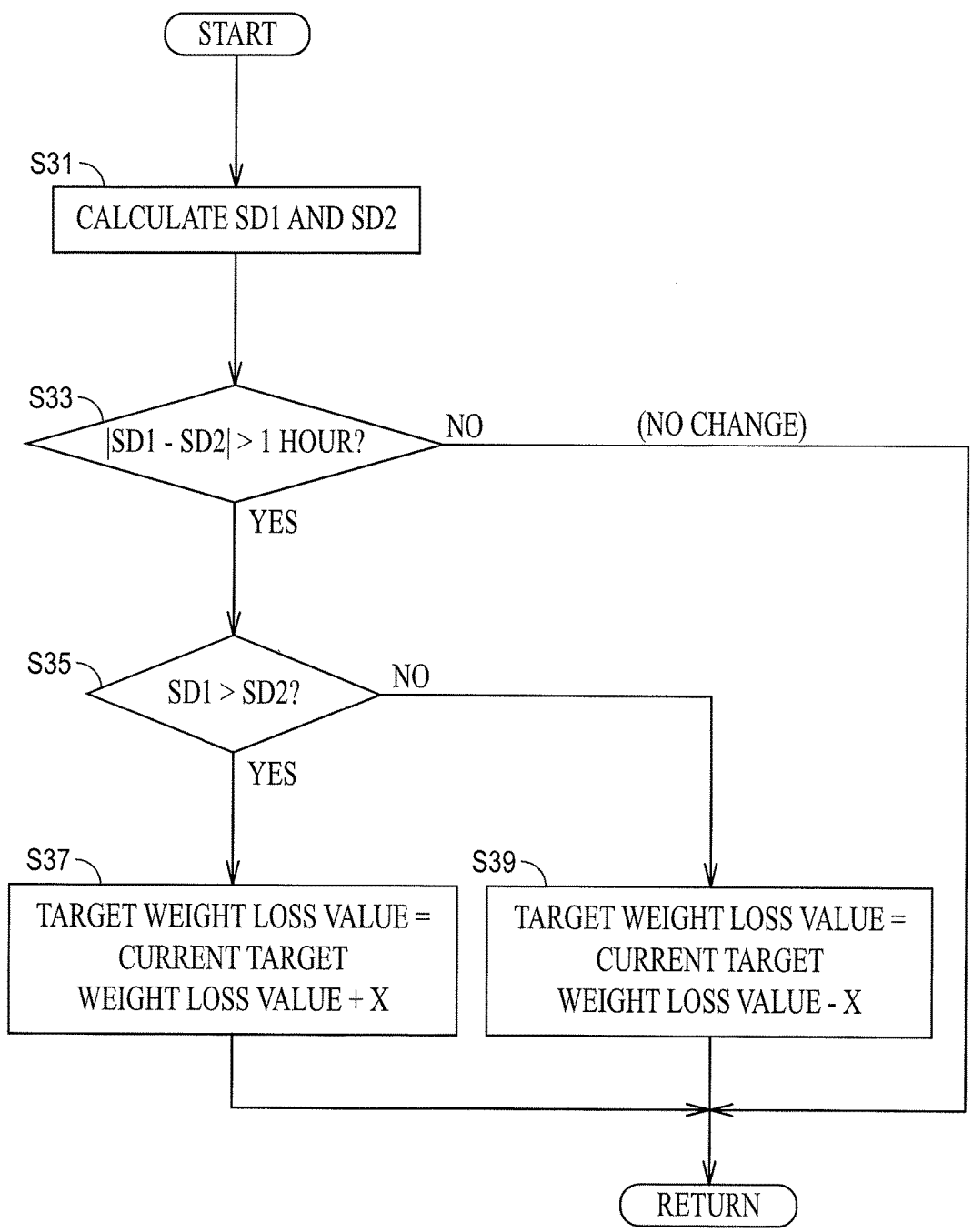
FIG. 8 is a flowchart illustrating another analysis process according to an embodiment of the present invention.

FIG. 6 is a main flowchart illustrating processing executed by the CPU 181 of the control unit 18 in the body weight/body composition meter 3, whereas FIGS. 7 and 8 are flowcharts illustrating an analysis process for updating the intra-day target weight loss value data 41. These flowcharts are held in a memory in the control unit 18 or the storage unit 12 in advance as programs, and the processes are realized by the CPU 181 reading out the programs and executing the commands contained therein.

Note that the intra-day target weight loss value data 41 through the analysis process execution day data 46 shown in FIGS. 5A through 5G are assumed to be set in the storage unit 12.

Furthermore, it is assumed that the measurement subject has measured his/her body weight once each day at the evening time, and thus a sufficient number of instances of the measurement data 40 spanning from the date indicated by the target setting day data 42, such as the past 21 days (three weeks), is already stored in the storage unit 12. Accordingly, it is assumed that the evening body weight on the twenty-first day is measured through the processing in the flowchart shown in FIG. 6.

As shown in FIG. 6, the CPU 181 starts up in response to the measurement subject inputting a power on instruction through the operating unit 14 (step S1), and, using the load detection unit 33, measures the body weight of the measurement subject who has stepped onto the upper surface cover unit 35 (see FIG. 1) (step S5).

At this time, the CPU 181 calculates the body composition information based on the impedance detected by the impedance detection unit 20 (see FIG. 2) using the electrode units 36 of the body weight measurement unit 30 and the electrode units 21 of the display/operating unit 10. Meanwhile, the body weight obtainment unit 62 and the impedance obtainment unit 72 input the measured body weight value and the detected impedance value from the double integral AD unit 19. These inputted values are associated with each other and stored in the storage unit 12 by the body weight holding unit 64 and the impedance holding unit 74 as the data 401 and 404. The loss amount data 402 obtained by the change obtainment unit 66 and the measurement date/time data 403 based on time data from the timer unit 13 are also associated and stored with the aforementioned data. Through this, measurement data 40 resulting from the current body weight measurement is stored in the storage unit 12 (step S8).

In order to determine whether or not to execute the analysis process (step S11; mentioned later), the CPU 181 compares time data from the timer unit 13 with the date indicated by the target setting day data 42 and the date indicated by the analysis process execution day data 46, and based on a result of the comparison, determines whether or not the date indicated by the time data is a date after a predetermined period (for example, 11 days) has passed from the date indicated by the target setting day data 42 or the analysis process execution day data 46 (step S9).

In the case where it is determined that the date indicated by the time data is a date after the predetermined period has passed (YES in step S9), the analysis process is executed by the CPU 181 (step S11), the evening body weight value for the next day (called the "target value" hereinafter) is calculated (step S12), and information including the target value is displayed in the display unit 15 (step S13). Thereafter, the CPU 181 turns the power off (step S15), thus ending the processing.

On the other hand, in the case where it is determined that the date indicated by the time data is not a date after the predetermined period has passed (NO in step S9), the process of step S11 is skipped, the processes of steps S12, S13, and S15 are executed, and the series of processes then ends.

Analysis Process

Next, the analysis process (see step S11 in FIG. 6) will be described with reference to FIG. 7. The intra-day target weight loss value data 41 for calculating the target value is obtained in the analysis process.

First, the achievement rate obtainment unit 68 calculates the target achievement rate using the measurement data 40 stored in the storage unit 12 (step S21).

Specifically, based on the time data from the timer unit 13 and the measurement time data 403, the measurement data 40 of the most recent predetermined period is selected (extracted) from the measurement data 40 in the storage unit 12, and the loss amount data 402 is read out from the selected measurement data 40. The values in the read-out loss amount data 402 are compared to the value indicated by the intra-day target weight loss value data 41, and based on a result of the comparison, the target is determined to be "achieved" in the case where the body weight loss amount is greater than or equal to the value indicated by the intra-day target weight loss value data 41 and is determined to be "not achieved" in the case where the body weight loss amount is less than the value indicated by the intra-day target weight loss value data 41. The result of the determination is stored in a table 121 in a predetermined region of the storage unit 12. Through this, a determination result indicating whether the weight loss target has been achieved or has not been achieved is obtained for each day in the most recent predetermined period.

FIG. 9A illustrates an example of the table 121. In the table 121, the loss amount data 402 and a determination result 122 indicating whether the weight loss target has been achieved or has not been achieved are stored in association with each other, for each day in the most recent predetermined period (that is, 11 days), in the case where the intra-day target weight loss value data 41 indicates 40 g, for example.

The achievement rate obtainment unit 68 calculates the target achievement rate based on the determination results 122 in the table 121. In other words, the target achievement rate, indicating the percentage of days, in a total number of days in the most recent predetermined period (that is, 11 days), in which a determination of "achieved" has been made, is calculated. According to the content of FIG. 9A, the target achievement rate is calculated as 20%.

When the target achievement rate is obtained, the CPU 181 determines whether or not the target achievement rate is less than a predetermined threshold (50%, for example) (step S23). In the case where it is determined that the target achievement rate is less than the predetermined threshold (YES in step S23), the target obtainment unit 70 for updating the intra-day target weight loss value data 41 in the storage unit 12 is launched, and the intra-day target weight loss value data 41 in the storage unit 12 is updated (step S25). After this, the procedure returns to the processing in FIG. 6. Note that the threshold is not limited to 50%.

When updating the intra-day target weight loss value data 41, the target obtainment unit 70 updates (overwrites) the value of the intra-day target weight loss value data 41 in the storage unit 12 to a new value so that the target achievement rate becomes greater than or equal to 50%. Specifically, based on a difference between the obtained target achievement rate and the predetermined threshold (50%), the weight gain/loss obtainment unit 71 calculates a weight gain/loss amount for updating the intra-day target weight loss value data 41 using a predetermined arithmetic expression. This arithmetic expression is an expression that derives a value so that the value of the intra-day target weight loss value data 41 decreases as the stated difference increases, and is an expression for calculating the intra-day target weight loss value data 41 so as to avoid excessive weight loss. Accordingly, here, the weight gain/loss obtainment unit 71 obtains a value for reduction (that is, a negative value).

The target obtainment unit 70 calculates a new intra-day target weight loss value data 41 value by adding the calculated weight gain/loss amount to the current intra-day target weight loss value data 41 value, and updates the intra-day target weight loss value data 41 in the storage unit 12 using the calculated new value.

On the other hand, in the case where it is determined that the target achievement rate is greater than or equal to the predetermined threshold (50%) (NO in step S23), the intra-day target weight loss value data 41 in the storage unit 12 is not updated, or in other words, the process of step S25 is skipped and the procedure returns to the processing shown in FIG. 6.

Returning to FIG. 6, the CPU 181 calculates a target value for the evening body weight measurement carried out the next day, by subtracting the value of the intra-day target weight loss value data 41 in the storage unit 12 from the body weight measured in step S5 (step S12). The calculated target value is held in the measurement data 40 in association with the other data.

The CPU 181 supplies the calculated target value and the intra-day target weight loss value data 41 read out from the storage unit 12 to an output processing unit 548. The output processing unit 548 displays the target value and the intra-day target weight loss value data 41 value in the display unit 15 (step S13). The power is then turned off (step S15). Through this, the series of processes ends.

Next, a change in the determination result 122 in the analysis process (step S11) will be described, assuming a case where the target obtainment unit 70 has overwritten the value of the intra-day target weight loss value data 41 in the storage unit 12 to "30 g". In the case where the value has been overwritten to "30 g", a determination result 122 such as that shown in (B) of FIG. 9 can be obtained even in the case where the value of the loss amount data 402 in the table 121 is the same value as in (A) in FIG. 9, and thus a target achievement rate of "60%" can be obtained. Accordingly, a high target achievement rate can be obtained even in the case where a weight loss pace similar to the pace followed before the update is maintained as a result of the updated new intra-day target weight loss value data 41 value; this makes it easy for the measurement subject to stay motivated to lose weight.

Figure 9:
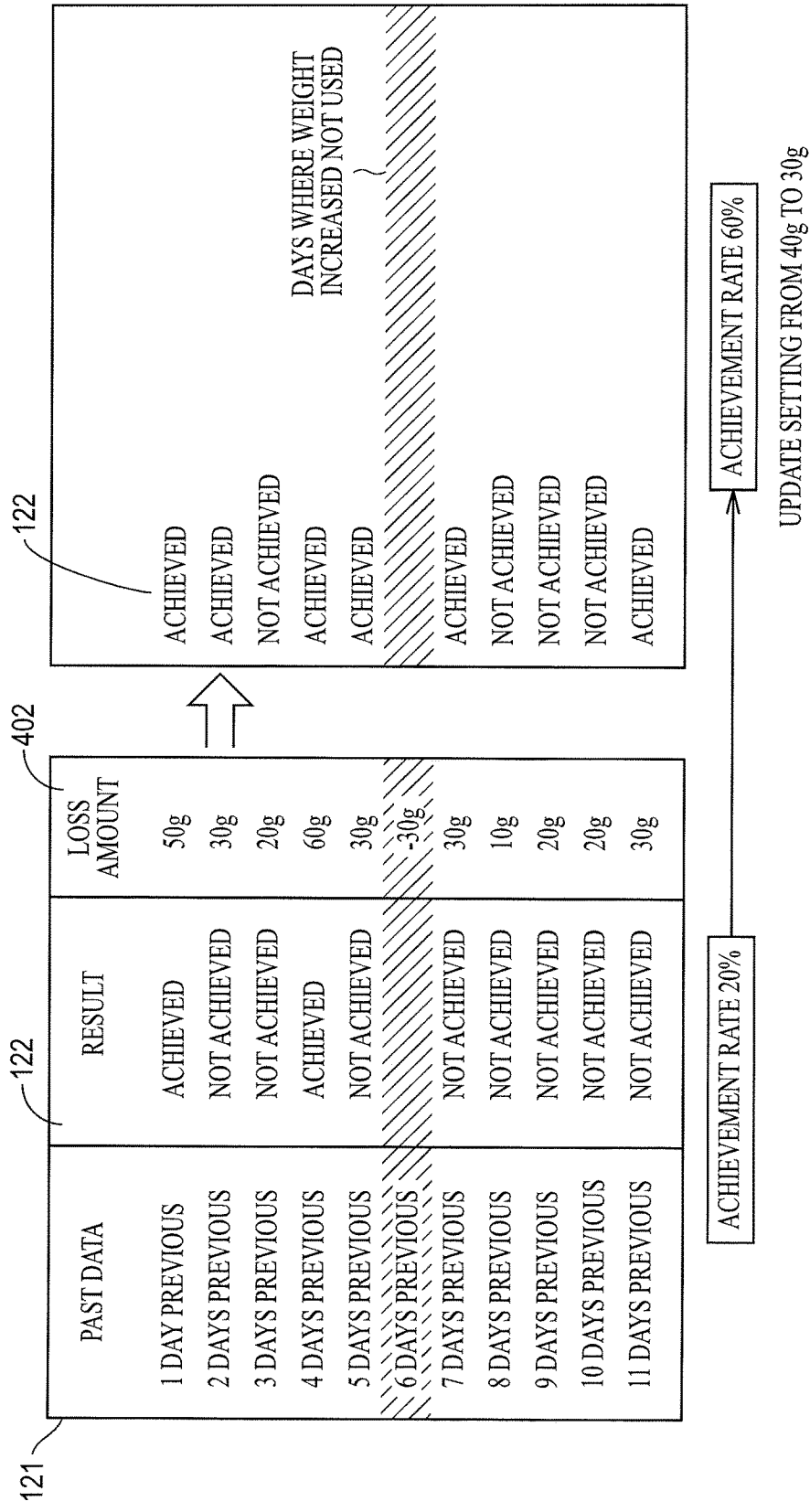
FIG. 9 is a diagram illustrating an example of a table according to an embodiment of the present invention.

Note that in FIG. 9, the measurement data 40 from days on which the body weight increased is not used in the target achievement rate calculation.

Figure 10:
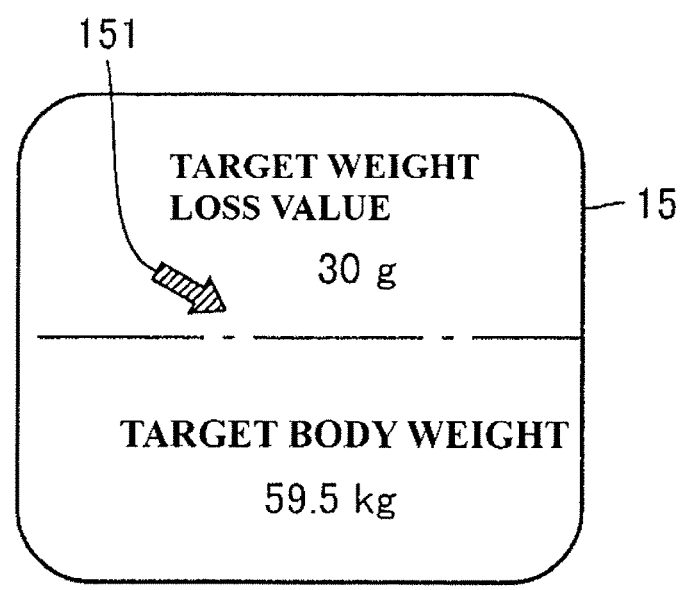
FIG. 10 is a diagram illustrating a display example according to an embodiment of the present invention.

FIG. 10 illustrates an example of the display performed in step S13. In FIG. 10, an arrow 151 indicates a result of comparing the target achievement rate to the predetermined threshold (50%). In other words, the arrow 151 is displayed pointing downward in the case where the target achievement rate is less than the threshold. This enables the measurement subject to confirm that the weight loss is not progressing favorably. On the other hand, the arrow 151 is displayed pointing upward in the case where the target achievement rate is greater than or equal to the threshold. This enables the measurement subject to confirm that the weight loss is progressing favorably, which makes it easy for the measurement subject to stay motivated to lose weight.

Note that the information for displaying the target achievement rate is not limited to the arrow 151. For example, the calculated target achievement rate may be displayed in the screen shown in FIG. 10.

Furthermore, the body weight value measured in step S5 may be displayed in the screen shown in FIG. 10, and the pre- and post-update intra-day target weight loss value data 41 values may be displayed in order to make it easy to stay motivated to lose weight.

In the analysis process shown in FIG. 7, the intra-day target weight loss value data 41 value is updated so as to decrease only in the case where the target achievement rate is less than the threshold; however, the value of the intra-day target weight loss value data 41 may be updated even in the case where the target achievement rate is greater than or equal to the threshold, with the intra-day target weight loss value data 41 value being updated so as to increase, for example.

Figure 11:
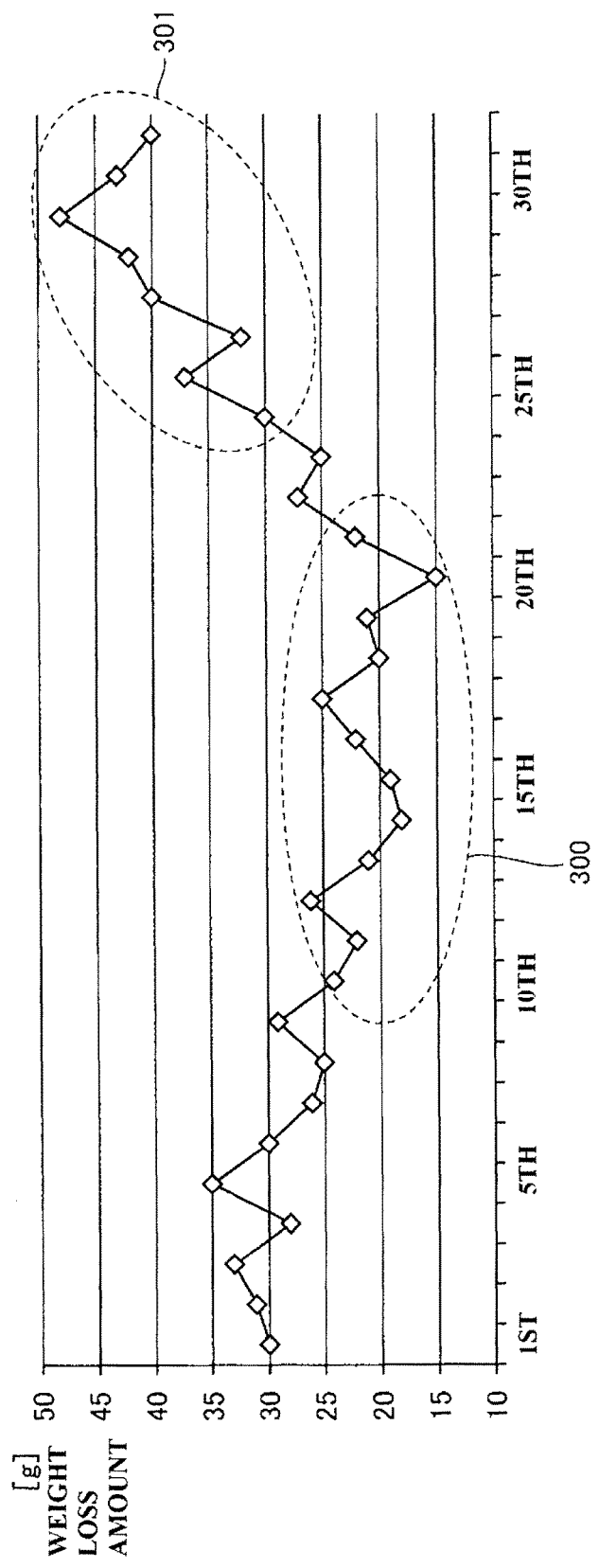
FIG. 11 is a graph illustrating changes in weight loss amounts according to an embodiment of the present invention.

Updating of the target achievement rate through the analysis process shown in FIG. 7 will be described with reference to the graph shown in FIG. 11, indicating weight loss change amounts. In the graph in FIG. 11, the vertical axis represents weight loss amounts, whereas the horizontal axis represents time. A period corresponding to an area 300 in the graph has intra-day target weight loss value data 41 of "30 g", and indicates a period of a low target achievement rate. Accordingly, based on the analysis process in FIG. 7, the intra-day target weight loss value data 41 value is updated to "20 g", for example. A period corresponding to an area 301 in the graph that follows thereafter represents a period where the weight loss progresses favorably and the target achievement rate is high, and thus the intra-day target weight loss value data 41 ("20 g") is updated to "40 g", for example.

According to the analysis process shown in FIG. 7, the target achievement rate is calculated using the current intra-day target weight loss value data 41 every predetermined period, and in the case where the calculated target achievement rate is low, a new intra-day target weight loss value data 41 to serve as a target for future body weight measurement is obtained; this makes it easy for the measurement subject to stay motivated to lose weight, or in other words, makes it possible to obtain intra-day target weight loss value data 41 through which the target can be achieved. Accordingly, the intra-day target weight loss value data 41 can be updated so as to conform to the rhythm of the measurement subject's body weight changes.

Other Example of Analysis Process

The analysis process for updating the intra-day target weight loss value data 41 is not limited to the process using the target achievement rate shown in FIG. 7; information expressing the regularity of the measurement subject's lifestyle can be used for the update as well.

The information expressing the regularity of the measurement subject's lifestyle is obtained by the regularity obtainment unit 76. Specifically, from the measurement data 40 stored in the storage unit 12, the regularity obtainment unit 76 selects (extracts) the measurement data 40 from the most recent predetermined period (the past three weeks, for example), based on the time data from the timer unit 13. A variation SD1 in the time indicated by the data 403 in the selected measurement data 40 from the past three weeks and a variation SD2 in the time indicated by the data 403 in the measurement data 40 from the most recent seven days (for example, the past seven days) are calculated, and the measurement subject's lifestyle regularity is derived from the difference between the two (that is, SD1−SD2). Here, the variations SD1 and SD2 are assumed to be calculated based on standard deviations.

The aforementioned difference is sufficiently low in the case where the body weight measurement time is essentially constant in the most recent predetermined period, but is not sufficiently low in the case where the body weight measurement time varies greatly. Accordingly, whether or not the measurement subject's lifestyle is regular can be determined based on this difference. The regularity obtainment unit 76 determines whether or not the difference is great by comparing the difference with a threshold (one hour, for example).

Another example of the analysis process (see step S11 in FIG. 6) that employs the regularity obtainment unit 76 will be described with reference to FIG. 8.

First, from the measurement data 40 in the storage unit 12, the regularity obtainment unit 76 selects (extracts) the measurement data 40 whose date indicated by the data 403 is from the past three weeks, based on the time data from the timer unit 13. The aforementioned variations SD1 and SD2 are then calculated based on the measured body weight indicated by the data 401 in the selected measurement data 40 (step S31).

The regularity obtainment unit 76 calculates the difference between the variations SD1 and SD2 and determines whether or not the difference is greater than the threshold (one hour, for example) (step S33). In the case where it is determined that the difference is less than or equal to the threshold (NO in step S33), the process ends without the intra-day target weight loss value data 41 being updated, and the procedure returns to the processing in FIG. 6. In other words, in the case where the difference is less than or equal to the threshold and is sufficiently low, the measurement subject's lifestyle is regular and thus the weight loss is progressing favorably. In this case, in the present embodiment, the processing for updating the intra-day target weight loss value data 41 in the storage unit 12 so as to maintain the weight loss pace (the processes in steps S37 and S39) is omitted.

On the other hand, in the case where it is determined that the difference is greater than the threshold (YES in step S33), the intra-day target weight loss value data 41 is updated (steps S35, S37, and S39). Specifically, the regularity obtainment unit 76 determines whether or not a conditional expression (SD1>SD2) for determining the update method holds true (step S35), and outputs a result of the determination to the target obtainment unit 70.

In the case where the result of the determination indicates that the conditional expression holds true (YES in step S35), the target obtainment unit 70 updates the intra-day target weight loss value data 41 in the storage unit 12 by adding a predetermined value X (5 g, for example) thereto (step S37). As a result, the intra-day target weight loss value data 41 in the storage unit 12 is overwritten so as to increase. Meanwhile, in the case where the result of the determination indicates that the conditional expression does not hold true (NO in step S35), the target obtainment unit 70 updates the intra-day target weight loss value data 41 in the storage unit 12 by subtracting the predetermined value X therefrom (step S39). As a result, the intra-day target weight loss value data 41 in the storage unit 12 is overwritten so as to decrease.

In this manner, periods of easy weight loss and periods of difficult weight loss are estimated from the measurement subject's lifestyle regularity, which is based on the variations SD1 and SD2; the intra-day target weight loss value data 41 is updated based on that estimation, and as a result it is easy for the measurement subject to stay motivated to lose weight.

Although the predetermined value X is a static value here, it should be noted that the predetermined value X may be variable. In other words, the weight gain/loss obtainment unit 71 may vary the value to add to or subtract from the intra-day target weight loss value data 41 based on the difference between the variations SD1 and SD2.

Other Method for Obtaining Lifestyle Regularity

Although the measurement subject's lifestyle regularity is obtained based on the body weight measurement time in the data 403 in the foregoing, the regularity may instead be obtained based on the impedance data 404.

Body impedance is known to be affected by changes in body composition such as body water amount, fat amount, and the like. If the measurement subject's lifestyle is regular, the amount of water that enters the body from the exterior can be considered essentially constant; meanwhile, body composition types aside from the water amount do not undergo short-term changes. Accordingly, if the measurement subject's daily diet is regular, the body impedance value measured at the same time each day will not vary greatly; however, if the daily diet becomes irregular due to changes in time spans for meals or meal content (such as water content), the impedance value will vary greatly even if the body impedance is measured at the same time.

Accordingly, in the present embodiment, a variation may be calculated using the impedance data 404 in the measurement data 40, as shown in FIG. 8; the lifestyle regularity may then be obtained based on the calculated regularity and the intra-day target weight loss value data 41 may be updated based on the regularity.

Meanwhile, if the measurement subject's lifestyle in general becomes irregular, his/her daily diet will be disrupted and the data 403 (that is, the evening time when the evening body weight is measured) will vary as well, and thus the target obtainment unit 70 may employ, as the new intra-day target weight loss value data 41, an average of a new intra-day target weight loss value data 41 calculated using the variation in the measurement time and a new intra-day target weight loss value data 41 calculated using the variation in the impedance value.

Other Example of Changing Intra-Day Target Weight Loss Value

It is known that the loss amount data 402 changes based on the measurement subject's lifestyle patterns. For example, in cases such as where the measurement subject works on weekdays and takes weekends off, it is difficult to lose weight on weekdays, when the measurement subject is involved in deskwork or the like, but easier to lose weight on days off, when the measurement subject is more active. Accordingly, in the case where a set lifestyle pattern is repeated cyclically, the intra-day body weight change value indicated by the loss amount data 402 also changes cyclically. Accordingly, the intra-day target weight loss value data 41 may be varied based on cyclic changes in the intra-day body weight change value of the measurement subject.

Specifically, the regularity obtainment unit 76 extracts a time-series change pattern for the loss amount data 402, based on the past measurement data 40 stored in the storage unit 12. Periods where the loss amount data 402 value is comparatively high and periods where the loss amount data 402 value is comparatively low are determined from the extracted change pattern, and the intra-day target weight loss value data 41 value used for calculating the target value is changed based on the period that has been determined.

Figure 12:
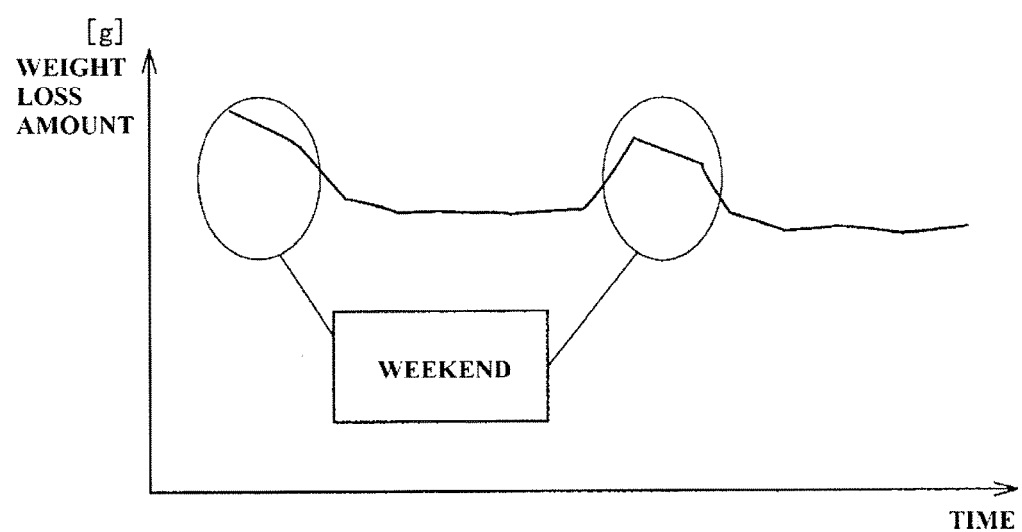
FIG. 12 is another graph illustrating changes in weight loss amounts according to an embodiment of the present invention.

FIG. 12 is a graph indicating changes over time in the value of the loss amount data 402 according to the present embodiment. In FIG. 12, the vertical axis represents weight loss amounts, whereas the horizontal axis represents time. The regularity obtainment unit 76 obtains the time-series change graph shown in FIG. 12 based on the data 401 and 403 in the measurement data 40 stored in the storage unit 12, and extracts a regularity of the cyclical change in the intra-day body weight change value from the obtained graph. The regularity obtainment unit 76 obtains, from the graph in FIG. 12, days of the week on which the weight loss amount is greater than other days of the week (Saturday and Sunday, for example) as the regularity.

The target obtainment unit 70 calculates an average value of the loss amount data 402 on the days of the week on which the weight loss amount is great (50 g, for example) and an average value of the loss amount data 402 on other days of the week (20 g, for example) based on the regularity obtained by the regularity obtainment unit 76 and the data of the graph in FIG. 12, and obtains those values as the intra-day target weight loss value data 41.

Accordingly, based on the time data from the timer unit 13, the CPU 181 calculates the target evening body weight according to the formula (previous day's evening body weight)−(50 g) when it is determined that the target evening body weight to be calculated is an evening body weight from days of the week on which the weight loss amount is great, and calculates the target evening body weight according to the formula (previous day's evening body weight)−(20 g) when it is determined that the target evening body weight to be calculated is an evening body weight from another day of the week.

Through this, in the case where the measurement subject cyclically repeats a set lifestyle pattern, the intra-day target weight loss value can be varied according to that lifestyle pattern, and thus it is easy for the measurement subject to stay motivated to lose weight.

Meanwhile, the intra-day target weight loss value for calculating the target value may be determined by finding an average of the value of the intra-day target weight loss value data 41 varied according to the lifestyle pattern in this manner and the value of the intra-day target weight loss value data 41 updated based on the regularity as shown in FIGS. 7 and 8.

Variations

Although the evening body weight is obtained each day as the body weight measured during a single measurement and the next day's evening body weight is obtained as the target value in the aforementioned embodiment, the morning body weight may be measured instead. In other words, the morning body weight may be measured, and the next day's morning body weight may be obtained as the target value using the same method as described in the aforementioned embodiment. A measurement result such as that shown in FIG. 10 can be displayed even in the case where the morning body weight is measured.

Furthermore, both the morning body weight and the evening body weight may be measured each day, and the next day's morning body weight may be obtained and displayed as the target value when the morning body weight is measured, whereas the next day's evening body weight may be obtained and displayed as the target value when the evening body weight is measured.

Other Embodiments

Although all of the processes for body weight management are carried out by the body weight/body composition meter 3 in the aforementioned embodiment, the configuration may be such that the processes are executed by the server 5 instead of the body weight/body composition meter 3. Functions of the server 5 will be described hereinafter.

In the case where such processes are executed by the server 5, the body weight/body composition meter 3 sends the measurement data 40 to the server 5 when carrying out the process for storing the measurement data 40 in step S8. Then, the CPU 521 in the control unit 52 of the server 5 obtains the measurement data 40 from the body weight/body composition meter 3 and executes processing according to the aforementioned flowcharts. Data is stored in the storage unit 55, and information is displayed in the display unit 54 instead of the display unit 15.

The server 5 may send the information displayed in the screen of the display unit 54 to the body weight/body composition meter 3. The body weight/body composition meter 3 may receive this information from the server 5 and display the received information in the display unit 15. The server 5 may also send the information displayed in the screen of the display unit 54 to a mobile terminal such as a measurement subject's PDA (personal digital assistant). The measurement subject can then confirm the information on the display of the mobile terminal when s/he is away.

The functional configuration of the server 5, as related to body weight management, will be described with reference to FIG. 4. FIG. 4 illustrates functions of the CPU 521 as well as peripheral circuitry related thereto.

The CPU 521 includes an operation acceptance unit 530 that accepts a user operation via the operating unit 53 and outputs an operation signal based on the accepted operation; a body weight obtainment unit 532 that obtains the measurement data 40 sent from the body weight/body composition meter 3; a body weight holding unit 534 for holding the obtained measurement data 40 in a predetermined region of the storage unit 55; a change obtainment unit 536; an achievement rate obtainment unit 538; the target obtainment unit 540 that has a weight gain/loss obtainment unit 541; an impedance obtainment unit 542; an impedance holding unit 544; a regularity obtainment unit 546; the output processing unit 548 for displaying information in the display unit 54; and a communication processing unit 550 for communicating with external devices, including the body weight/body composition meter 3, via the communication unit 51. These elements have the same functions as the corresponding elements in FIG. 3.

The elements in FIG. 4 are realized by programs executed by the CPU 521. These programs are stored in advance in a ROM (not shown) of the control unit 52. The functions of the respective elements are realized by the CPU 521 reading out the programs from the ROM and executing the commands in the read-out programs. The programs may be downloaded by the communication unit 51 from an external device such as a server (not shown), stored in the storage unit 55, and read out from the storage unit 55 and executed by the CPU 521.

Meanwhile, in the aforementioned embodiment, a body fat percentage, BMI (body mass index), visceral fat level, skeletal muscle percentage, body age, and so on may be calculated based on the measurement subject's impedance detected by the impedance detection unit 20, the height, age, and sex of the measurement subject stored in the storage unit 12, and the body weight detected by the load detection unit 33, and that calculated information may be outputted along with the body weight.

Furthermore, the stated body weight management method carried out by the body weight/body composition meter 3 according to the present embodiment can also be provided as a program. This program can also be temporarily recorded on a computer-readable recording medium, such as a flexible disk, a CD-ROM (compact disk read-only memory), a ROM, a RAM, a memory card, and so on provided to the computer of the control unit 18 or the control unit 52, and can then be provided as a program product. Alternatively, the program can be recorded on a recording medium such as a hard disk mounted within a computer, and can be provided in such form as a program. Further still, the program can also be downloaded via a network, and can be provided in such form as a program.

The provided program product is installed in a program storage unit such as a hard disk or the like and is then read out and executed by the CPU 181 (or 521). Note that the program product includes the program itself and the recording medium on which the program is recorded.

Note that the embodiments disclosed above are to be understood as being in all ways exemplary and in no way limiting. The scope of the present invention is defined not by the aforementioned descriptions but by the scope of the appended claims, and all changes that fall within the same essential spirit as the scope of the claims are intended to be included therein as well.

REFERENCE SIGNS LIST

1 body weight management system
3 body weight/body composition meter
5 server
18, 52 control unit
20 impedance detection unit
30 body weight measurement unit
40 measurement data
41 intra-day target weight loss value data
46 analysis process execution day data
60, 530 operation acceptance unit
62, 532 body weight obtainment unit
64, 534 body weight holding unit
66, 536 change obtainment unit
68, 538 achievement rate obtainment unit
70, 540 target obtainment unit
71, 541 weight gain/loss amount obtainment unit
72, 542 impedance obtainment unit
74, 544 impedance holding unit
76, 546 regularity obtainment unit
78, 548 output processing unit
80, 550 communication processing unit
121 table
122 determination result
151 arrow
401, 403, 404 data
402 loss amount data
SD1, SD2 variation

The invention claimed is:

1. A body weight management system that actively updates a display to keep a target weight loss goal up-to-date, the system comprising:
a body weight/body composition meter including:
the display;
first electrodes and second electrodes;
a memory; and
a processor configured to:
obtain and store in the memory body weight values of a measurement subject from the first electrodes and the second electrodes;
obtain and store in the memory a date/time for each of the body weight values, which is the date/time that the body weight value is obtained; and
set a single-day target weight loss value representing a target of weight loss to be achieved per day;
each day of a predetermined number of days: (A) obtain and store in the memory, from the first and second electrodes, a current body weight value and a date/time of the measurement; (B) determine a loss amount which is the remaining difference when a current body weight value is subtracted from a body weight value of the measurement subject obtained on a day before the preselected day; (C) compare the loss amount with the single-day target weight loss value; and (D) determine that the target: (i) is achieved when the loss amount is greater than or equal to the single-day target weight loss value, and (ii) is not achieved when the loss amount is less than the single-day target weight loss value;
determine an achievement rate which is a percentage of days that the target is achieved out of the predetermined number of days;
update the single-day target weight loss value to be reduced when the achievement rate is less than a predetermined threshold; and
control the display to display the updated target weight loss value, whereby a user of the body weight management system is provided with an actively-updated, visibly perceptible target weight loss goal.

2. The body weight management system according to claim 1, wherein the processor is further configured to:
obtain a weight gain/loss amount of the single-day target weight loss value based on a magnitude of the remaining difference; and
update the stored value of the single-day target weight loss value based on the single-day target weight loss value employed in the comparison and the obtained weight gain/loss amount.

3. The body weight management system according to claim 2, wherein the processor is further configured to:
obtain information expressing how regular the measurement subject's lifestyle is; and
obtain the weight gain/loss amount of the single-day target weight loss value based on the obtained information expressing how regular the measurement subject's lifestyle is.

4. The body weight management system according to claim 3, wherein the processor is further configured to:
obtain the information expressing how regular the measurement subject's lifestyle is based on the obtained measurement date/time.

5. The body weight management system according to claim 3, wherein the processor is further configured to:
obtain a daily body impedance value of the measurement subject; and
obtain the information expressing how regular the measurement subject's lifestyle is based on the obtained daily body impedance value.

6. The body weight management system according to claim 3, wherein the processor is further configured to obtain the information expressing how regular the measurement subject's lifestyle is from time-series information indicating a change over time in the single-day weight change value.

7. The body weight management system according to claim 1, wherein the processor is further configured to control the display to display information indicating the obtained target achievement rate.

8. The body weight management system according to claim 1, wherein the updated stored value of the single-day target weight loss value increases when the obtained achievement rate is greater than or equal to the threshold achievement rate.

9. The body weight management system according to claim 1, wherein the processor is further configured to update the stored value of the single-day target weight loss value to a new value based on a magnitude of the difference between the obtained achievement rate and a threshold achievement rate in such a manner that the value of the stored value of the single-day target weight loss value data decreases as the magnitude of the difference increases.

10. The body weight management system according to claim 1, wherein the predetermined threshold is 50%.

11. The body weight management system according to claim 1, wherein the
body weight/body composition meter further includes:
a display/operating housing member, that is configured to be held by a measurement subject and that:
houses the display; and
provides the first electrodes on surfaces of grip portions of the display/operating housing member, the grip portions being configured to be held in the measurement subject's hand, and configured to apply high-frequency current, supplied from a power source, to palms of the measurement subject's hands that are gripping the grip portions; and
a body weight measurement housing member onto which the measurement subject steps, which provides the second electrodes in a surface of an upper surface area of the body weight housing member, wherein the second electrodes are configured to detect a current that flows from soles of the measurement subject's feet, the second electrodes including a set of four electrodes that make contact with the left toe side, the left heel side, the right toe side, and the right heel side of the measurement subject's feet.

12. The body weight management system according to claim 1, wherein the processor is configured to: update the single-day target weight loss value so that an achievement rate for the predetermined number of days would be greater than or equal to 50%.

\* \* \* \* \*